US00PP20582P2

(12) United States Plant Patent
Smith

(10) Patent No.: US PP20,582 P2
(45) Date of Patent: Dec. 15, 2009

(54) ***BRACHYCOME* PLANT NAMED 'ENDURING BLUE'**

(50) Latin Name: *Brachycome angustifolia*
Varietal Denomination: Enduring Blue

(75) Inventor: Kimberley K. Smith, Mt. Eliza (AU)

(73) Assignee: Outback Plants Pty. Ltd., Cranbourne, Victoria (AU)

( * ) Notice: Subject to any disclaimer, the term of this patent is extended or adjusted under 35 U.S.C. 154(b) by 0 days.

(21) Appl. No.: 12/287,349

(22) Filed: Oct. 8, 2008

(51) Int. Cl.
*A01H 5/00* (2006.01)

(52) U.S. Cl. ..... Plt./411

(58) Field of Classification Search ..... Plt./263, Plt./411

See application file for complete search history.

*Primary Examiner*—Susan B McCormick Ewoldt
(74) *Attorney, Agent, or Firm*—C. A. Whealy

(57) ABSTRACT

A new and distinct cultivar of *Brachycome* plant named 'Enduring Blue', characterized by its compact and mounding plant habit; freely branching growth habit; freely flowering habit; large inflorescences positioned just above the foliage; purple violet-colored ray florets that resist fading; and good postproduction longevity.

1 Drawing Sheet

Botanical designation: *Brachycome angustifolia.*
Cultivar denomination: 'Enduring Blue'.

BACKGROUND OF THE INVENTION

The present invention relates to a new and distinct cultivar of *Brachycome*, botanically known as *Brachycome angustifolia* and hereinafter referred to by the name 'Enduring Blue'.

The new *Brachycome* plant is a product of a controlled breeding program conducted by the Inventor in Cranbourne, Victoria, Australia. The objective of the breeding program is to create new compact *Brachycome* plants with large inflorescences.

The new *Brachycome* originated from a cross-pollination in November, 2004 in Cranbourne, Victoria, Australia, of *Brachycome angustifolia* 'Billabong Mauve Delight', disclosed in U.S. Plant Pat. No. 10,899, as the female, or seed, parent with an unnamed selection of *Brachycome angustifolia*, not patented, as the male, or pollen, parent. The new *Brachycome* was discovered and selected by the Inventor as a single flowering plant from within the progeny of the stated cross-pollination in a controlled environment in Cranbourne, Victoria, Australia in March, 2005.

Asexual reproduction of the new *Brachycome* by vegetative cuttings in a controlled environment in Cranbourne, Victoria, Australia since May, 2005 has shown that the unique features of this new *Brachycome* are stable and reproduced true to type in successive generations.

SUMMARY OF THE INVENTION

Plants of the new *Brachycome* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Enduring Blue'. These characteristics in combination distinguish 'Enduring Blue' as a new and distinct cultivar of *Brachycome:*

1. Compact and mounding plant habit.
2. Freely branching growth habit.
3. Freely flowering habit.
4. Large inflorescences positioned just above the foliage.
5. Purple violet-colored ray florets that resist fading.
6. Good postproduction longevity.

Plants of the new *Brachycome* differ from plants of the female parent, 'Billabong Mauve Delight', in the following characteristics:

1. Plants of the new *Brachycome* are taller than plants of 'Billabong Mauve Delight'.
2. Plants of the new *Brachycome* have thicker stems than plants of 'Billabong Mauve Delight'.
3. Plants of the new *Brachycome* have larger inflorescences than plants of 'Billabong Mauve Delight'.
4. Plants of the new *Brachycome* and 'Billabong Mauve Delight' differ in ray floret color as plants of 'Billabong Mauve Delight' have light purple-colored ray florets.

Plants of the new *Brachycome* differ from plants of the male parent selection in the following characteristics:

1. Plants of the new *Brachycome* are larger than plants of the male parent selection.
2. Plants of the new *Brachycome* have thicker stems than plants of the male parent selection.
3. Plants of the new *Brachycome* have larger inflorescences than plants of the male parent selection.
4. Plants of the new *Brachycome* and the male parent selection differ in ray floret color as plants of the male parent selection have pale purple violet-colored ray florets.

Plants of the new *Brachycome* can also be compared to plants of the *Brachycome multifida* 'Metallic Blue', disclosed in U.S. Plant Pat. No. 13,692. In side-by-side comparisons conducted in Cranbourne, Victoria, Australia, plants of the new *Brachycome* differed from plants of 'Metallic Blue' in the following characteristics:

1. Plants of the new *Brachycome* were more compact than plants of 'Metallic Blue'.

2. Plants of the new *Brachycome* had thicker stems than plants of 'Metallic Blue'.
3. Plants of the new *Brachycome* and 'Metallic Blue' differed in ray floret color as plants of 'Metallic Blue' had light violet-colored ray florets.

BRIEF DESCRIPTION OF THE PHOTOGRAPH

The accompanying colored photograph illustrates the overall appearance of the new *Brachycome,* showing the colors as true as it is reasonably possible to obtain in colored reproductions of this type. Colors in the photograph may differ slightly from the color values cited in the detailed botanical description which accurately describe the colors of the new *Brachycome*. The photograph comprises a close-up view of a typical flowering plant of 'Enduring Blue' grown in a container.

DETAILED BOTANICAL DESCRIPTION

The aforementioned photograph and following observations, measurements and values describe plants grown in 15-cm containers in Cranbourne, Victoria, Australia, under commercial practice during the spring, summer and autumn in a polyethylene-covered greenhouse with day temperatures ranging from 12° C. to 40° C., night temperatures ranging from 6° C. to 28° C. and light levels ranging from 1,000 lux to 9,000 lux. Plants were pinched about four to six weeks after planting. Plants had been growing for four months when the photograph was taken and about five months when the description was taken. In the following description, color references are made to The Royal Horticultural Society Colour Chart, 1995 Edition, except where general terms of ordinary dictionary significance are used.

Botanical classification: *Brachycome angustifolia* 'Enduring Blue'.

Parentage:

*Female, or seed, parent.*—*Brachycome angustifolia* 'Billabong Mauve Delight', disclosed in U.S. Plant Pat. No. 10,889.

*Male, or pollen, parent.*—Unnamed selection of *Brachycome angustifolia,* not patented.

Propagation:

*Type.*—By vegetative cuttings.

*Time to initiate roots, summer.*—About 10 to 20 days at temperatures of 20° C. to 25° C.

*Time to initiate roots, winter.*—About 18 to 30 days at temperatures of 18° C. to 20° C.

*Time to produce a rooted young plant, summer.*—About four to six weeks at temperatures of 20° C. to 35° C.

*Time to produce a rooted young plant, winter.*—About five to eight weeks at temperatures of 10° C. to 20° C.

*Root description.*—Thin, slightly fleshy; white in color.

*Rooting habit.*—Freely branching; moderately dense.

Plant description:

*Plant form/habit.*—Compact and mounded plant habit; moderately vigorous growth habit. Freely branching habit with numerous lateral branches developing after pinching.

*Plant height.*—About 25 cm to 30 cm.

*Plant width* (*spread*).—About 40 cm to 60 cm.

*Lateral branches.*—Length: About 3 cm to 6.5 cm. Diameter: About 1.5 mm. Internode length: About 3 mm to 15 mm. Strength: Moderately strong. Texture: Smooth, glabrous. Color: Close to 137A to 137B.

Foliage description:

*Arrangement.*—Alternate, simple; sessile.

*Length.*—About 9 mm to 54 mm.

*Width.*—About 4 mm to 22 mm.

*Shape.*—Narrowly to broadly wedge-shaped.

*Apex.*—Acute to somewhat obtuse.

*Base.*—Attenuate.

*Margin.*—Three to five-lobed.

*Texture, upper and lower surfaces.*—Smooth, glabrous.

*Venation pattern.*—Pinnate.

*Color.*—Developing leaves, upper surface: Close to 137A. Developing leaves, lower surface: Close to 137C. Fully expanded leaves, upper surface: Close to 139A; venation, 139A. Fully expanded leaves, lower surface: Close to 137C; venation, close to 137C.

Inflorescence description:

*Appearance.*—Single composite inflorescence form with ray and disc florets. Inflorescences borne just above the foliage. Freely flowering habit with numerous inflorescences developing per plant during the flowering period.

*Fragrance.*—Very faintly fragrant; sweet.

*Flowering season.*—Plants flower from spring through autumn in Australia; flowering continuous during this period. Plants begin flowering about four to eight weeks after planting.

*Inflorescence longevity.*—Inflorescences last about two to four weeks on the plant; inflorescences not persistent.

*Inflorescence bud.*—Height: About 1 mm to 2 mm. Diameter: About 2 mm to 3 mm. Shape: Oblate. Color: Close to 137B.

*Inflorescence size.*—Diameter: About 2.2 cm to 3 cm. Diameter of disc: About 4 mm to 8 mm.

*Ray florets.*—Quantity/arrangement: About 19 to 24 in about two whorls. Shape: Lanceolate, narrowly oblong. Apex: Bluntly acute. Base: Attenuate. Margin: Entire. Length: About 7 mm to 11 mm. Width: About 1.5 mm to 2 mm. Texture, upper and lower surfaces: Smooth, glabrous. Color: When opening, upper surface: Close to 87B. When opening, lower surface: Close to 58A. Fully opened, upper surface: Close to 81C to 81D; color becoming closer to 76A with development. Fully opened, lower surface: Close to 76A.

*Disc florets.*—Arrangement: Massed at center of receptacle. Shape: Tubular, elongated. Apex: Five-pointed. Length: About 3 mm. Width: About 1 mm. Texture: Smooth, glabrous. Color, immature: Close to 144A Color, mature: Close to 12A.

*Involucral bracts.*—Quantity/arrangement: About 12 to 16 arranged in one to two whorls; bracts imbricate. Length: About 2 mm to 3 mm. Width: About 1 mm. Shape: Oblong. Apex: Acute to obtuse. Margin: Entire, fringed. Texture, upper and lower surfaces: Smooth, glabrous; satiny. Color, upper and lower surfaces: Close to 138B.

*Peduncles.*—Length, terminal peduncle: About 3.8 cm to 7.2 cm. Diameter: About 2 mm. Strength: Moderately strong. Texture: Smooth, glabrous. Color: Close to 138A.

*Reproductive organs.*—Present on disc florets only. Androecium: Filament length: Less than 1 mm. Filament color: Close to 155D. Anther length: Less than 1 mm. Anther shape: Oblong to lanceolate. Pollen amount: Moderate. Gynoecium: Stigma shape: Bilobed. Style length: About 3 mm. Style color: Close to 155D.

*Seeds.*—Seed set is nil to scarce on plants of the new *Brachycome*. Quantity per inflorescence: None to about three. Length: Less than 1 mm. Diameter: Less than 1 mm.

Disease/pest resistance: Plants of the new *Brachycome* have been observed to be tolerant to Powdery Mildew. Plants of the new *Brachycome* have not been observed to be resistant to pests and other pathogens common to *Brachycomes*.

Garden performance: Plants of the new *Brachycome* have been observed to have good garden performance and tolerate rain, wind and temperatures ranging from about −3° C. to about 40° C.

It is claimed:

1. A new and distinct *Brachycome* plant named 'Enduring Blue' as illustrated and described.

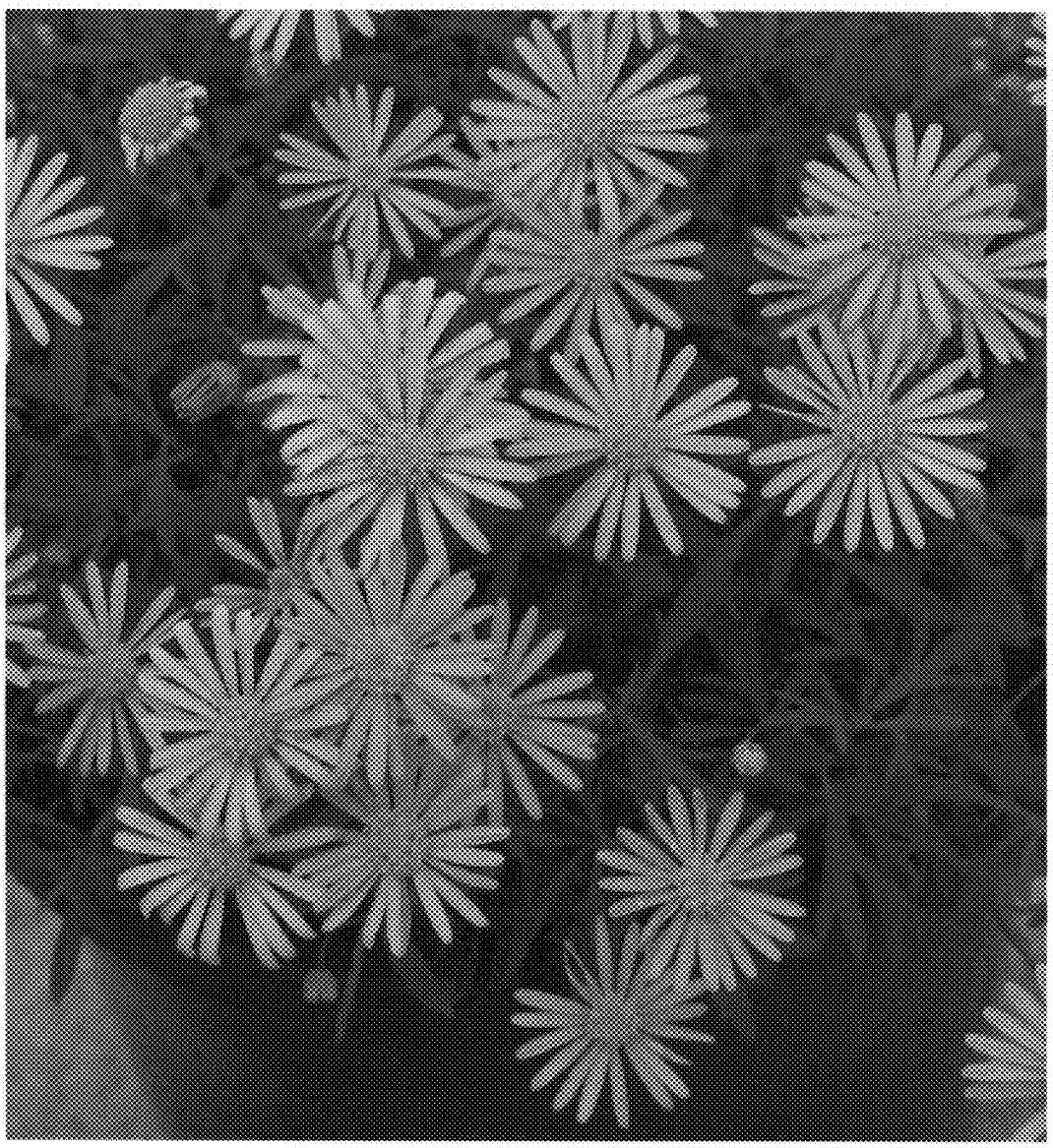

* * * * *